United States Patent
Reever et al.

(10) Patent No.: US 12,102,375 B2
(45) Date of Patent: Oct. 1, 2024

(54) SYSTEMS AND METHODS FOR TISSUE COAGULATION

(71) Applicant: BOSTON SCIENTIFIC SCIMED, INC., Maple Grove, MN (US)

(72) Inventors: Kenneth Reever, Hopedale, MA (US); Richard Tah, Milford, MA (US); Jozef Slanda, Milford, MA (US); Aditi Ray, Palo Alto, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 596 days.

(21) Appl. No.: 16/434,273

(22) Filed: Jun. 7, 2019

(65) Prior Publication Data
US 2019/0374276 A1  Dec. 12, 2019

Related U.S. Application Data

(60) Provisional application No. 62/682,603, filed on Jun. 8, 2018.

(51) Int. Cl.
*A61B 18/14* (2006.01)
*A61B 17/00* (2006.01)
(Continued)

(52) U.S. Cl.
CPC .......... *A61B 18/14* (2013.01); *A61B 18/1206* (2013.01); *A61B 18/20* (2013.01);
(Continued)

(58) Field of Classification Search
CPC . A61B 18/1492; A61B 18/1206; A61B 18/14; A61B 18/20; A61B 18/24;
(Continued)

(56) References Cited

U.S. PATENT DOCUMENTS 5,401,272 A * 3/1995 Perkins ................. A61B 18/24
606/50
5,403,311 A 4/1995 Abele et al.
(Continued)

FOREIGN PATENT DOCUMENTS

EP 0900549 A1 3/1999
EP 1989991 A1 11/2008
EP 1620025 B1 10/2011

OTHER PUBLICATIONS

Office Action for counterpart Chinese Application No. 201980039073.2 dated Jun. 14, 2024 (10 pages).

*Primary Examiner* — Khadijeh A Vahdat
*Assistant Examiner* — Marina Delaney Templeton
(74) *Attorney, Agent, or Firm* — Bookoff McAndrews PLLC

(57) ABSTRACT

A medical device may include a handle having a handle lumen extending therethrough. The medical device further may include a first body shaft including a first body shaft lumen in direct communication with the handle lumen and an RF electrode tip may be positioned at a distal end of the first body shaft. The RF electrode tip may include a lumen extending therethrough and in direct communication with the lumen of the first body shaft. Additionally, an energy delivery wire may be electrically coupled with the RF electrode tip.

20 Claims, 6 Drawing Sheets

(51) Int. Cl.
   *A61B 18/00*    (2006.01)
   *A61B 18/12*    (2006.01)
   *A61B 18/20*    (2006.01)

(52) U.S. Cl.
   CPC ............... *A61B 17/00234* (2013.01); *A61B 2018/00589* (2013.01); *A61B 2018/00595* (2013.01); *A61B 2018/00625* (2013.01); *A61B 2018/1253* (2013.01); *A61B 2018/126* (2013.01); *A61B 2018/144* (2013.01)

(58) Field of Classification Search
   CPC .............. A61B 18/22; A61B 18/201; A61B 2018/00589; A61B 2018/00595; A61B 2018/1253; A61B 2018/126; A61B 2018/0091; A61B 2018/00994; A61B 2018/00625; A61B 2018/144; A61B 2018/00196; A61B 2018/1405; A61B 2018/2015; A61B 2018/20357; A61B 2018/2205; A61B 2018/2211; A61B 2018/2255; A61B 2018/1233; A61B 2018/2238; A61B 2017/22074; A61B 2017/22078
   See application file for complete search history.

(56) References Cited

U.S. PATENT DOCUMENTS

| | | | |
|---|---|---|---|
| 5,413,029 A | 5/1995 | Gent et al. | |
| 5,437,662 A * | 8/1995 | Nardella | A61B 18/1206 606/50 |
| 5,445,142 A | 8/1995 | Hassler, Jr. | |
| 5,486,161 A | 1/1996 | Lax et al. | |
| 5,514,131 A * | 5/1996 | Edwards | A61N 1/403 606/41 |
| 5,518,501 A | 5/1996 | Oneda et al. | |
| 6,517,498 B1 | 2/2003 | Burbank et al. | |
| 7,226,444 B1 * | 6/2007 | Ellman | A61B 18/22 606/41 |
| 8,216,229 B2 * | 7/2012 | Elliott | A61B 17/12181 606/41 |
| 8,360,968 B2 | 1/2013 | Hadani | |
| 8,398,540 B2 | 3/2013 | Hassidov et al. | |
| 8,870,752 B2 | 10/2014 | Avitsian et al. | |
| 9,498,108 B1 | 11/2016 | Lombardi | |
| 9,810,844 B2 | 11/2017 | Reever | |
| 9,854,959 B2 | 1/2018 | Levy et al. | |
| 11,712,149 B2 | 8/2023 | Lu et al. | |
| 2003/0181904 A1 | 9/2003 | Levine et al. | |
| 2004/0225286 A1 | 11/2004 | Elliott | |
| 2004/0267257 A1 * | 12/2004 | Bourne | A61B 18/1487 606/41 |
| 2010/0057072 A1 | 3/2010 | Roman et al. | |
| 2013/0267943 A1 * | 10/2013 | Hancock | H05B 6/806 606/33 |
| 2013/0274614 A1 * | 10/2013 | Shimada | A61B 5/0205 600/587 |
| 2013/0317491 A1 * | 11/2013 | Fukuda | A61B 18/1492 606/16 |
| 2015/0327913 A1 * | 11/2015 | Horner | A61B 18/1492 606/41 |
| 2016/0324576 A1 * | 11/2016 | Ebbutt | A61B 18/1815 |
| 2017/0143414 A1 * | 5/2017 | Sliwa | A61B 18/1492 |
| 2017/0325886 A1 | 11/2017 | Graham et al. | |
| 2019/0374285 A1 * | 12/2019 | Hancock | A61B 1/07 |

\* cited by examiner

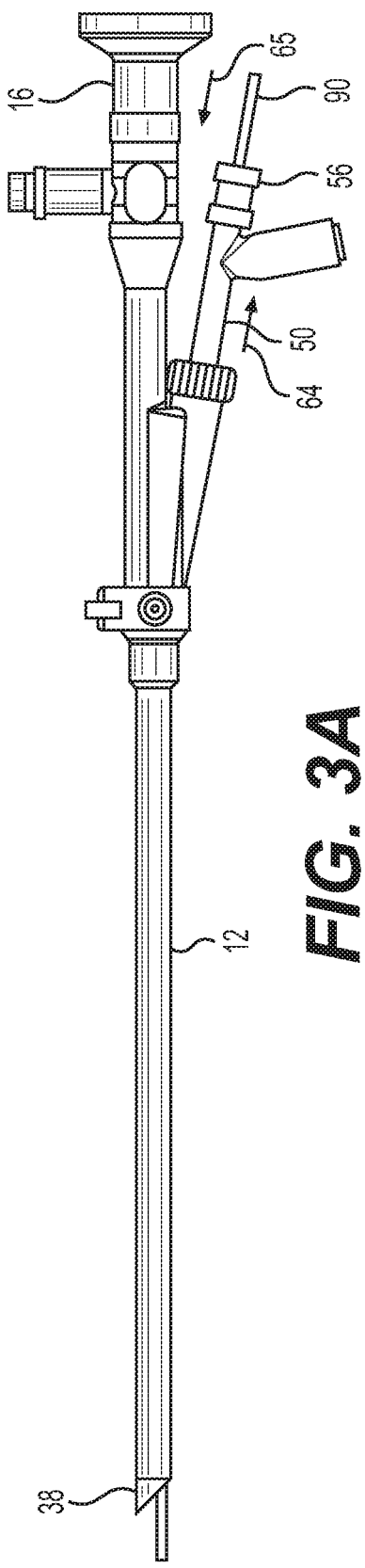
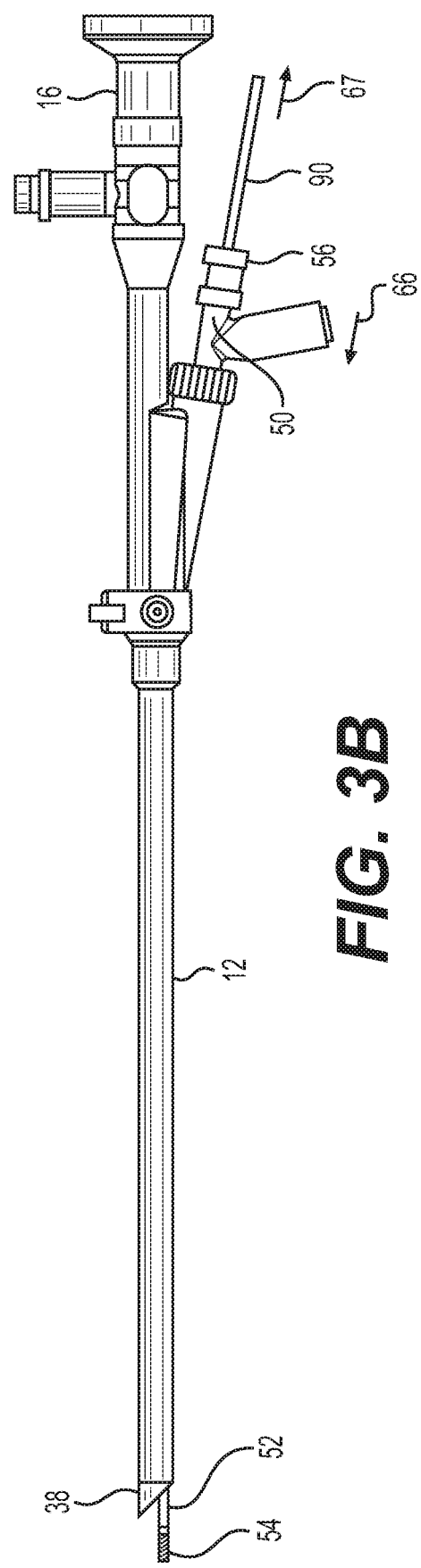

SYSTEMS AND METHODS FOR TISSUE COAGULATION

CROSS-REFERENCE TO RELATED APPLICATIONS

This patent application claims the benefit of priority under 35 U.S.C. § 119 to U.S. Provisional Patent Application No. 62/682,603, filed Jun. 8, 2018, which is herein incorporated by reference in its entirety.

TECHNICAL FIELD

The present disclosure relates generally to medical systems, devices, and related methods. More specifically, the present disclosure relates to medical systems and/or devices for treating tissue within the body of a patient.

BACKGROUND

Optical fibers may be used in medical laser systems to deliver a laser energy to a treatment site. Lasers have been used in, for example, urology, neurology, otorhinolaryngology, general anesthetic ophthalmology, dentistry, gastroenterology, cardiology, gynecology, thoracic, and orthopedic procedures. One example of a procedure that may be performed using a laser system is laser cautery of tissue to promote healing. Occasionally, laser fiber cautery may be less effective than RF electrocautery depending on specific patient anatomy. For example, laser fiber cautery, which interacts with blood hemoglobin, may not be as effective in cauterizing tissue as RF electrocautery which coagulates proteins in the tissue. Due to differences in modes of action, laser fiber cautery may not be as successful as RF electrocautery. In such cases, a medical professional may wish to remove a laser fiber device from an insertion device (e.g., endoscope) and insert an RF electrode. Removing the laser fiber device and then re-routing an RF electrode through an insertion device may add significant amounts of time, and therefore cost, to a medical procedure.

The systems, devices, and methods of the current disclosure may rectify some of the deficiencies described above or address other aspects of the prior art.

SUMMARY

Examples of the present disclosure relate to, among other things, medical devices. Each of the examples disclosed herein may include one or more of the features described in connection with any of the other disclosed examples.

A medical device may include a handle having a handle lumen extending therethrough. The medical device further may include a first body shaft including a first body shaft lumen in direct communication with the handle lumen and an RF electrode tip may be positioned at a distal end of the first body shaft. The RF electrode tip may include a lumen extending therethrough and in direct communication with the lumen of the first body shaft. Additionally, an energy delivery wire may be electrically coupled with the RF electrode tip.

The medical device may further include one or more of the following features. The energy delivery wire may extend along a radially exterior surface of the first body shaft toward the handle. The handle may further include a passage and the energy delivery wire may extend through the passage for connection with an RF generator. The medical device may further include a second body shaft defining a second body shaft lumen and the first body shaft may be received within the second body shaft lumen. The RF electrode tip may extend distally of the second body shaft. The energy delivery wire may be at least partially received within the second body shaft lumen of the second body shaft. The second body shaft may include an electrically insulating material. The RF electrode tip may include a pair of RF electrodes. The energy delivery wire may be a first energy delivery wire electrically coupled to a first electrode of the pair of RF electrodes, and the medical device may further include a second energy delivery wire electrically coupled to a second electrode of the pair of RF electrodes. Each of the first energy delivery wire and the second energy delivery wire may extend through a passage of the handle for connection with an RF generator plug. The pair of RF electrodes may be arranged for bipolar delivery of RF energy. The pair of RF electrodes may be electrically coupled for monopolar delivery of RF energy. The handle may further include an RF plug receptacle for connection with an RF generator. A proximal end of the handle lumen may include a tapered, flared, or chamfered surface. A sealing cap may be coupled to a proximal end of the handle.

In a further example, a method for energy delivery to tissue may include positioning an RF electrode tip of an energy delivery device in a first configuration distally of an insertion device positioned within the body of a patient. Additionally, the method may include delivering RF energy to tissue within the body of the patient via the RF electrode tip and ceasing delivery of RF energy via the RF electrode tip. Further, the method may include retracting the RF electrode tip to a location within a lumen of the insertion device in a second configuration and advancing a laser fiber through a lumen of the RF electrode tip and distally of the insertion device. The method may further include any one or more of the following features. The method may include delivering laser energy via the laser fiber. The method may include retracting the laser fiber to a location within the laser energy device. The method may include heat sinking the RF electrode tip to the insertion device in the second configuration.

In a further example, a system for energy delivery may include an insertion device including a lumen extending therethrough. Additionally, the system may include an RF energy delivery device including a handle, a first body shaft, and an RF electrode tip. Additionally, the RF energy device may include a lumen extending through the handle, the first body shaft, and the RF electrode tip. Additionally, a laser fiber may be at least partially received within the lumen of the RF energy delivery device.

Examples of the system may further include one or more of the following features. The RF electrode tip may include a pair of RF electrodes printed or chemically etched thereon. Additionally, a first energy delivery wire may be electrically coupled to a first electrode of the pair of RF electrodes, and a second energy delivery wire may be electrically coupled to a second electrode of the pair of RF electrodes, and each of the first energy delivery wire and the second energy delivery wire may extend along a radially exterior surface of the first body shaft toward the handle. The system may further include a second body shaft and at least a portion of the first body shaft may be positioned within a lumen of the second body shaft, and the RF electrode tip may extend distally of the second body shaft.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of the stated value unless otherwise stated.

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

FIG. 3A illustrates the exemplary medical system of FIG. 1 in a laser energy delivery configuration;

FIG. 3B illustrates the exemplary medical system of FIG. 1 in an RF energy delivery configuration.

DETAILED DESCRIPTION

Examples of the present disclosure relate to medical systems for treating internal areas of a patient's body. Each of the medical systems described herein may include a laser energy delivery device and an RF electrode device.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the patient or closer to a medical professional using the medical device or insertion device. In contrast, "distal" refers to a position relatively farther away from the medical professional using the medical device or insertion device, or closer to the interior of the patient.

Figure 1A:
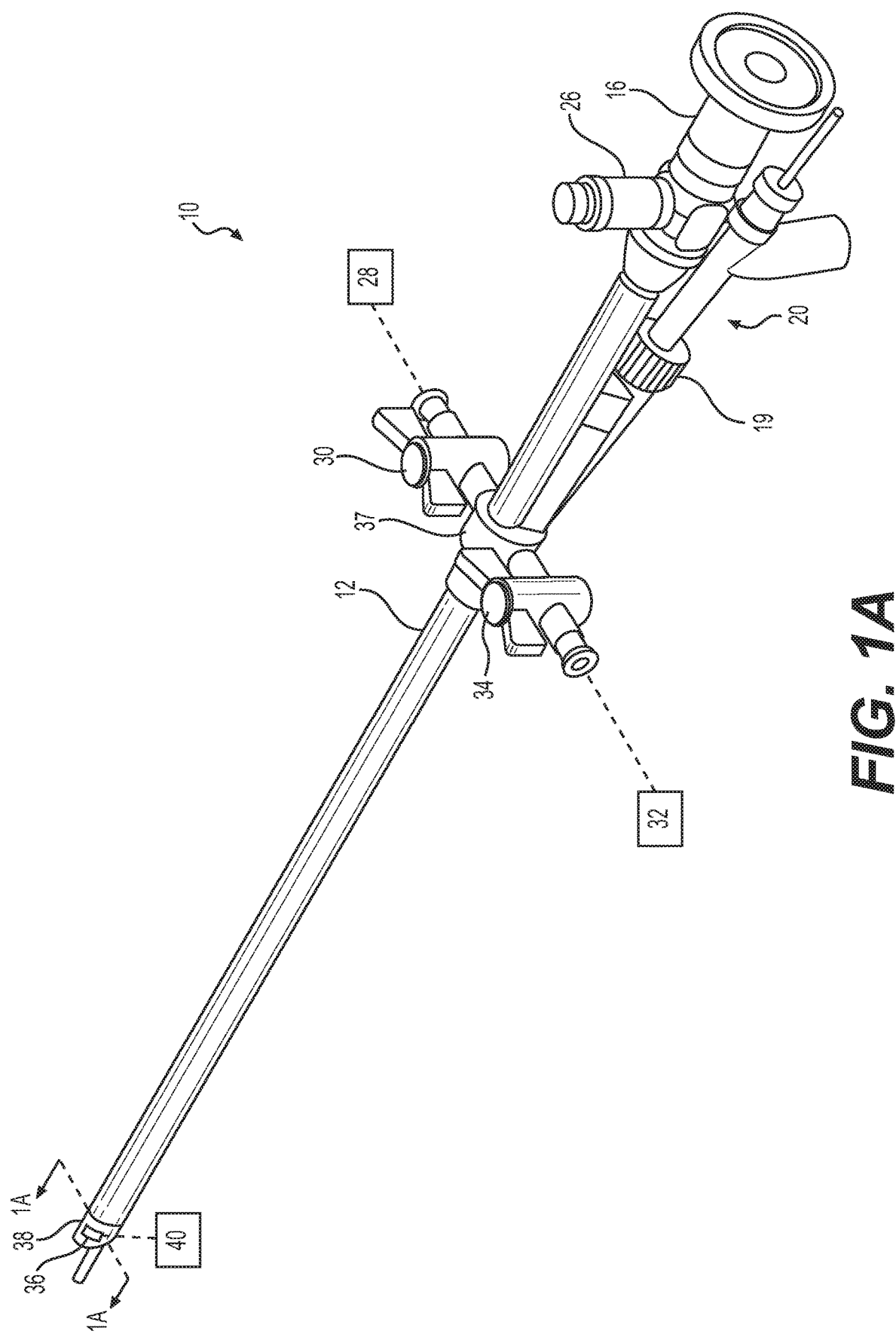
FIG. 1A illustrates an exemplary medical system according to the present disclosure.
Figure 1B:
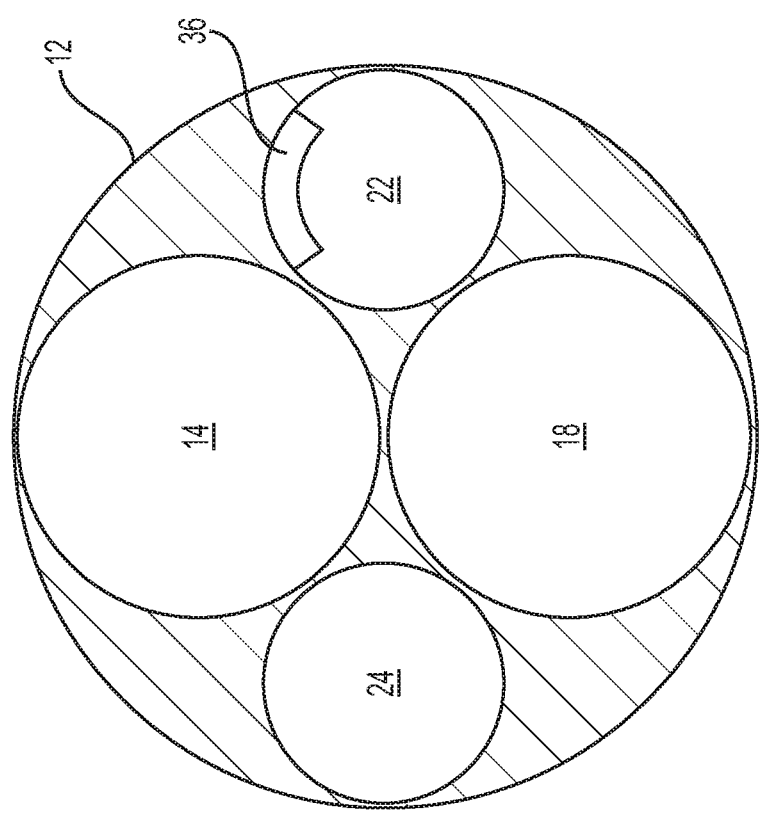
FIG. 1B is a cross-sectional view of the medical system of FIG. 1A taken at line 1A-1A.

FIG. 1A illustrates an exemplary medical system 10. Medical system 10 includes an insertion device 12. Insertion device 12 may include any device configured to allow a user to access and view internal areas of a subject's body such as, for example, a ureteroscope, a hysteroscope, a uteroscope, a bronchoscope, a cystoscope, and similar devices. Insertion device 12 may include a plurality of lumens extending therethrough. For example, as shown in FIG. 1B, insertion device 12 may include a first lumen 14 arranged for receiving an optics device 16, a second lumen 18 for receiving an RF electrode device 20, a third lumen 22, and a fourth lumen 24. It is understood that in some arrangements, insertion device 12 may include additional lumens not shown, or may not include at least third lumen 22 and/or fourth lumen 24, without departing from the scope of this disclosure.

Optics device 16 may include any appropriate device configured to provide a visual image of an internal location of a body of a patient. For example, optics device 16 may include one or more optical elements (e.g., lens, cameras, etc.) (not shown). Additionally, optics device 16 may include a receptacle 26 configured to receive a light cable so as to provide illumination light to the location within the body of the patient. Optics device 16 may be selectively inserted and removed from first lumen 14. Further, RF electrode device 20 may be selectively inserted, removed, or axially translated relative to second lumen 18, through a compression band 19, as will be described in further detail below. Additionally, third lumen 22 may be connected to a source of irrigation fluid 28 (e.g., water, saline, etc.) via stop cock 30, while fourth lumen 24 may be connected to a source of aspiration fluid 32 via stop cock 34. Each of third lumen 22 and fourth lumen 24 may originate at a connector hub 37 of insertion device 12 and terminate at the distal end of insertion device 12. In use, if it is deemed desirable or necessary, a medical professional may manually adjust one or both of stop cocks 30 and 34 to introduce irrigation fluid 28 and/or aspiration fluid 32, respectively. Optionally, in some arrangements, a sensor 36 may be arranged on (as shown in FIG. 1A) or within (as shown in FIG. 1B) a tip 38 of insertion device 12. Sensor 36 may sense one or both of a pressure or temperature at the location within the body of the patient, and may communicate with a controller 40 for automatically controlling delivery of one or more of irrigation fluid 28 or aspiration fluid 32. In such a case, stop cocks 30 and 34 may be omitted and delivery of irrigation fluid 28 and/or aspiration fluid 32 may be controlled via one or more valves (not shown) or the like.

Figure 2A:
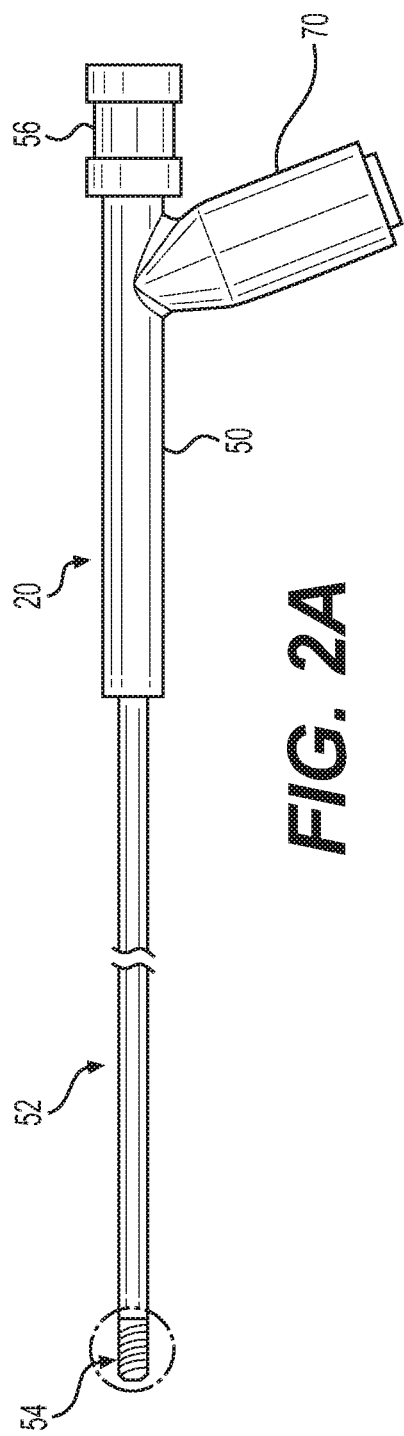
FIG. 2A illustrates an RF electrode device according to aspects of the present disclosure.
Figure 2B:
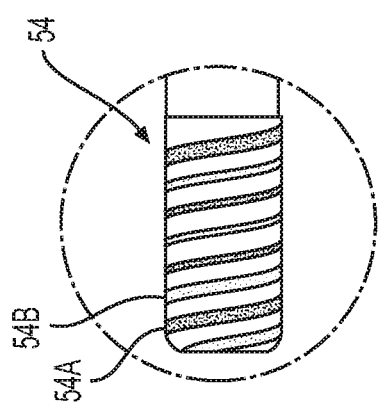
FIG. 2B illustrates an enlarged view of an electrode tip of the RF electrode device of FIG. 2A.
Figure 2C:
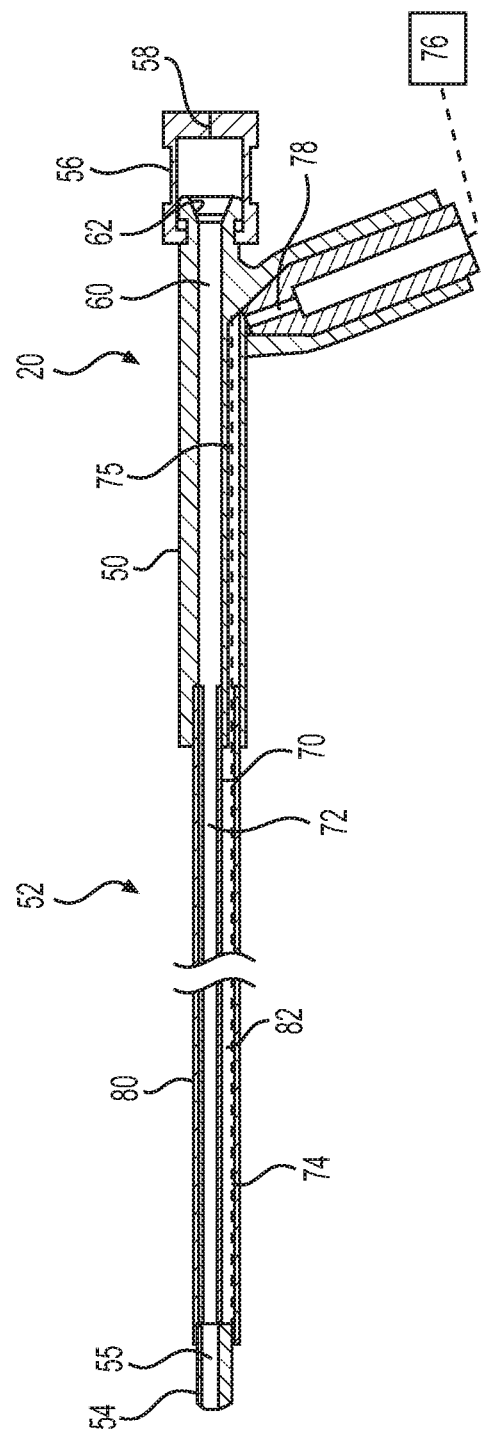
FIG. 2C is a cross-sectional view of the RF electrode device of FIG. 2A.

FIGS. 2A-2C illustrate RF electrode device 20. As shown, RF electrode device 20 includes a handle 50 and a body 52 terminating in an RF electrode 54. A sealing cap 56 may surround a proximal end of handle 50. As shown, sealing cap 56 may include a slit or opening 58 (FIG. 2C) extending therethrough such that one or more devices (e.g., laser fibers) may be inserted through sealing cap 56 and into a lumen 60 of handle 50. Sealing cap 56 may be formed of any appropriate material (e.g., polymer, silicon, etc.) arranged to flex, bend, or otherwise deform to enable insertion of one or more devices into lumen 60. In some arrangements, sealing cap 56 may retain a medical device in a particular axial location relative to lumen 60. That is, absent the application of a distally advancing (e.g., push) force or a proximally retracting (e.g., pull) force on a medical device within lumen 60, sealing cap 56 may hold or maintain a location of the medical device relative to handle 50. In addition, sealing cap 56 may be comprised of a material sufficient to prevent fluid from exiting proximally through slit 58. That is, sealing cap 56 may prevent leaking or passage of any fluid from a location distal of slit 58 to a location proximal of slit 58. In other arrangements, sealing cap 56 may be replaced with a seal and compression gland if so desired. As shown in FIG. 2C, for example, a proximal end of lumen 60 may include a tapered, chamfered, or flared opening 62 to assist a medical professional in delivering (e.g., guiding) a medical device (e.g., laser fiber) into lumen 60.

As shown in FIG. 2C, body 52 includes a first (e.g., inner) body shaft 70 defining a lumen 72 therein. Lumen 72 is in direct communication with lumen 60 of handle 50. That is, upon introduction of a medical device (e.g., laser device) through sealing cap 56, the medical device may be advanced through lumen 60 and into lumen 72. First body shaft 70 may be formed of a flexible material such as a polymer. A distal end of first body shaft 70 may terminate in RF electrode tip 54. RF electrode tip 54 may be tubular having a lumen 55 extending therethrough and may comprise a ceramic tip having only one (e.g., monopolar), or a pair of (e.g., bipolar) RF energy electrodes 54A, 54B. RF electrode tip 54 may be integrally formed with a distal end of first body shaft 70, or may be coupled to the distal end of first body shaft 70 in any appropriate manner (e.g., via an interference or other such fit) or adhesive bond.

Each electrode, e.g., 54A, 54B, may be additively inked on a ceramic substrate or applied by an etching removal process. Each electrode 54A, 54B may be connected to a source of RF energy via an electrically conductive line, lead, or wire 74 (e.g., only a single wire 74 is visible in FIG. 2C) extending proximally from RF electrode tip 54, along body 52, through a passage 75 of handle 50, and electrically coupled with an RF generator 76 via an RF plug receptacle 78. When activated, RF energy may be delivered from RF generator 76, in a bipolar arrangement, along body 52 via wires 74, to electrodes 54A and 54B (e.g., a first wire 74 may be electrically coupled with a first electrode 54A while a second wire 74 may be electrically coupled with a second electrode 54B). In a bipolar electrode arrangement, one of first electrode 54A or second electrode 54B is arranged as an energy delivery (e.g., hot) electrode while the other is arranged as a return electrode. Optionally, electrodes 54A and 54B may be electrically "shorted" (e.g., electrically connected) via a connection between wires 74 to form a monopolar energy deliver device. In such a case, an additional return electrode of RF generator 76 may be connected to the body of the patient (e.g., adhered to the skin of the patient). Alternatively, RF electrode tip 54 may include only one single electrode, e.g., electrode 54A, and only one wire 74. In this manner, electrode 54A is arranged as the energy delivery electrode, while an additional return electrode of RF generator 76 may be connected to the body of the patient (e.g., adhered to the skin of the patient).

In addition, body 52 includes a second (e.g., outer) body shaft 80. Second body shaft 80 may include a polymer sleeve, sheath, or film positioned about (e.g., encircling, surrounding, etc.) first body shaft 70 and wires 74. That is, second body shaft 80 defines a lumen 82 within which at least a portion of first body shaft 70 and wires 74 are received. Second body shaft 80 may electrically insulate body 52 and wires 74 from an interior surface of insertion device 12 (e.g., a surface of insertion device 12 defining second lumen 18) and may retain, hold, or otherwise secure wires 74 against a radially exterior surface of first body shaft 70. As shown, RF electrode tip 54 extends distally of second body shaft 80. Accordingly, RF energy may be delivered from RF generator 76, along one or both of wires 74, through tip 54, and toward tissue within the body of a patient without inadvertent shorting with one or more portions of insertion device 12.

In use, a medical professional may deem it medically necessary or desirable to deliver laser energy to tissue of a body of a patient. For example, the medical professional may deliver laser energy to treat benign prostate hyperplasia (BPH) to reduce the size of the prostate gland (e.g., by vaporizing tissue) and/or to cauterize tissue. In such an arrangement, as shown in FIG. 3A, medical system 10 may be arranged in a laser energy delivery configuration. In the laser energy delivery configuration, a laser fiber 90 may be passed through sealing cap 56, into lumen 60 (FIG. 2C) of handle 50, through lumen 72 of first body shaft 70, through lumen 55 of RF electrode tip 54, and distally of RF electrode tip 54, as indicated by arrow 65 in FIG. 3A. Meanwhile, RF electrode tip 54 may be proximally retracted as indicated via arrow 64 or otherwise received within second lumen 18 (FIG. 1B) of insertion device 12 and electrically isolated so as to prevent inadvertent electrical actuation. In such an arrangement, RF electrode tip 54 is not activated.

If the medical professional determines a need or desire to apply RF energy (e.g., so as to perform RF electrocautery of tissue), the medical professional may transition the system 10 to an RF energy delivery configuration, as shown in FIG. 3B. In such a manner, laser fiber 90 may be proximally retracted as shown via arrow 67 or otherwise positioned such that a distal tip thereof is received within lumen 72 of first body shaft 70. Additionally, RF energy device 20 (e.g., including handle 50, body 52, and RF electrode tip 54) may be distally advanced as shown via arrow 66 through second channel 18 of insertion device 12 such that at least RF electrode tip 54 is positioned distally of a tip 38 (or in arrangements in which tip 38 is not present, distally of a distal end face of body 52). Once so positioned, RF energy generator 76 may be activated so as to deliver RF energy through electrodes 54A, 54B to tissue. Due to the distal tip or end of laser fiber 90 being positioned within lumen 72 of first body shaft 70, laser fiber 90 is thermally protected from the effects of RF electrode tip 54 during delivery of RF energy to tissue of the patient. In such a manner, a medical professional may quickly transition between the laser energy delivery configuration (FIG. 3A) and the RF energy delivery configuration (FIG. 3B) of system 10, by proximal retraction 64 or distal advancement 66 or RF electrode device 20. Since the disclosed arrangement does not necessitate either of the RF energy device 20 nor laser fiber 90 to be completely removed during a procedure, the medical professional may reduce overall procedure time and cost, without forgoing the dual functionality of both RF energy delivery and laser energy delivery. In such a manner, a medical professional may dynamically tailor a medical procedure to adjust for individual patient needs.

Figure 4:
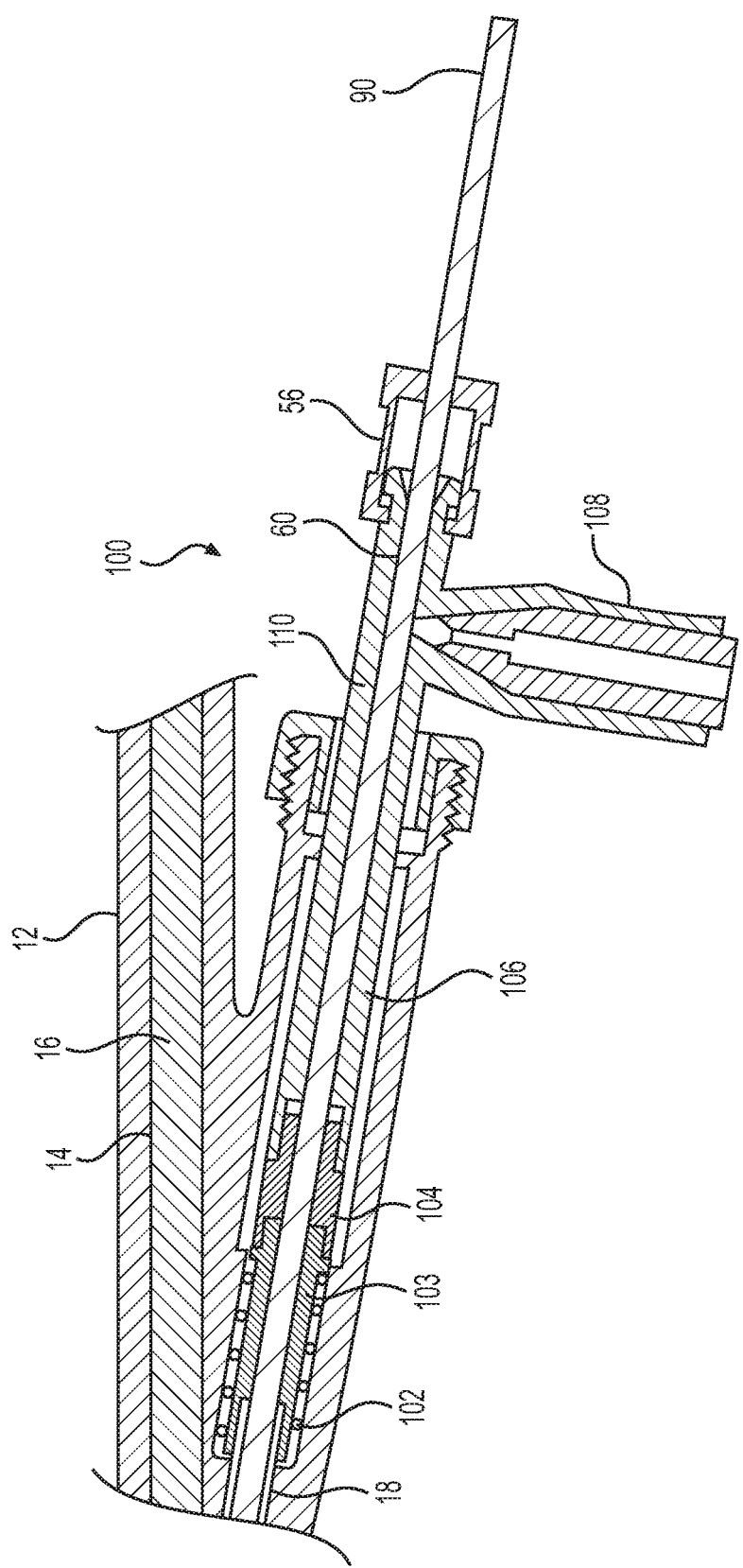
FIG. 4 is a cross-sectional view of an RF electrode device according to a further aspect of the present disclosure.

FIG. 4 is a cross-sectional view of an RF electrode device 100 according to a further aspect of the present disclosure. RF electrode device 100 is similar to electrode device 20, described above, and as such, similar components will be described and depicted with the same reference numerals. Notably, RF electrode device 100 differs from RF electrode device 20 in the manner of moving the RF electrode device 100 relative to insertion device 12. That is, rather than manually retracting RF electrode device 20 toward the laser energy delivery configuration of FIG. 3A or advancing the electrode device 20 toward the RF energy delivery configuration of FIG. 3B, RF electrode device 100 incorporates a cam arrangement to advance and retract RF electrode device 100. The cam arrangement operates in a fashion similar to that of a "click" pen writing instrument or the like and includes a biasing spring 102 positioned about a support member 103, an indexer 104, and a cam 106. Indexer 104 may include a plurality of v-shaped grooves arranged for contact with a plurality of v-shaped grooves of cam 106. Additionally, a radially exterior surface of cam 106 may include one or more protrusions configured to be received within, and slide distally and proximally relative thereto, a plurality of grooves positioned on an interior surface of insertion device 12. The grooves (not shown) of the insertion device 12 permit axial translation of cam 106 and a handle 110 of RF electrode device 100 while preventing rotation of cam 106 and handle 110 relative to insertion device 12. As in the case of a "click" pen writing instrument, a user may advance or retract RF electrode device 100 by application of a pushing force on a button, depression, or actuator 108 of handle 110 of RF electrode device 100. In so doing, spring 102 may be compressed and the v-shaped grooves of indexer 104 may rotate relative to the v-shaped grooves of cam 106, thereby adjusting an axial location of handle 110 of RF electrode device 100 relative to handle 110 to an extended axial position. A subsequent actuation of actuator 108 of handle 110 may again compress the spring and permit indexer 104 to rotate relative to cam 106 so as to return handle 110 of RF electrode device 100 to the initial axial position (e.g., a retracted axial position). Optionally, when RF electrode device 100 is retracted, there is a gap in an electrical connection between RF generator 76 and RF electrode 54 of RF electrode device 100. Due to the gap, no current will be permitted to flow from the RF generator 76 to the RF electrode tip 54. As such, an additional safety measure prevents inadvertent delivery of energy to the RF electrode tip 54 when in the laser energy delivery configuration (FIG. 3A).

Still further, in some arrangements, insertion device 12 may include an additional laser fiber lumen through which laser fiber 90 may extend. That is, instead of laser fiber 90 being delivered coaxially through lumen 60, 72, and RF electrode tip 54 as described above, laser fiber 90 may be arranged generally parallel to body 52 of RF electrode device 20.

Optionally, one or more of insertion device 12, RF electrode device 20, and optics device 16 may be either disposable for single use, or may be equipped for multiple uses. For example, in some arrangements, insertion device 12 may be a sterile single use component of system 10, while in other arrangements insertion device 12 may be reusable. In the case of a reusable insertion device 12, RF electrode device 20 may be a sterile single use component of system 10. Alternatively, other than RF electrode tip 54, RF electrode device 20 may be reusable. In such an arrangement, RF electrode tip 54 may be a sterile single use attachment for the remainder of RF electrode device 54.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A medical device, comprising:
a handle including a handle lumen extending therethrough;
a first body shaft including a first body shaft lumen in direct communication with the handle lumen;
a radio frequency (RF) electrode tip positioned at a distal end of the first body shaft, wherein the RF electrode tip includes a lumen extending therethrough and in direct communication with the lumen of the first body shaft; and
an energy delivery wire electrically coupled with the RF electrode tip,
wherein the RF electrode tip is a ceramic tip, and
wherein a laser fiber is positioned within the first body shaft lumen and the laser fiber is configured to extend distally to cauterize tissue and retract proximally relative to the RF electrode tip, the laser fiber being thermally protected from the RF electrode tip when retracted within the lumen.

2. The medical device of claim 1, wherein the energy delivery wire extends along a radially exterior surface of the first body shaft toward the handle.

3. The medical device of claim 1, wherein the handle further includes a passage, wherein the energy delivery wire extends through the passage for connection with an RF generator.

4. The medical device of claim 1, further including:
a second body shaft defining a second body shaft lumen, wherein the first body shaft is received within the second body shaft lumen.

5. The medical device of claim 4, wherein the RF electrode tip extends distally of the second body shaft.

6. The medical device of claim 4, wherein the energy delivery wire is at least partially received within the second body shaft lumen of the second body shaft.

7. The medical device of claim 4, wherein the second body shaft comprises electrically insulating material.

8. The medical device of claim 1, wherein the RF electrode tip includes a pair of RF electrodes, each RF electrode extending in a direction transverse to a longitudinal axis of the first body shaft.

9. The medical device of claim 8, wherein the energy delivery wire is a first energy delivery wire electrically coupled to a first electrode of the pair of RF electrodes, the medical device further including:
a second energy delivery wire electrically coupled to a second electrode of the pair of RF electrodes.

10. The medical device of claim 9, wherein each of the first energy delivery wire and the second energy delivery wire extends through a passage of the handle for connection with an RF generator plug.

11. The medical device of claim 8, wherein the pair of RF electrodes are arranged for bipolar delivery of RF energy.

12. The medical device of claim 8, wherein the pair of RF electrodes are electrically coupled for monopolar delivery of RF energy.

13. A medical device, comprising:
a handle including a handle lumen extending therethrough and an actuator;
a first body shaft including a first body shaft lumen in direct communication with the handle lumen;
an RF electrode tip positioned at a distal end of the first body shaft, wherein the RF electrode tip includes a lumen extending therethrough and in direct communication with the first body shaft lumen;
an RF generator electrically coupled with the RF electrode tip; and
an energy delivery wire electrically coupled with the RF electrode tip and the RF generator,
wherein the RF electrode tip includes a pair of RF electrodes printed or chemically etched thereon,
wherein the actuator is configured to axially extend and axially retract a distal portion of the handle relative to a proximal portion of the handle, and wherein, in the axially retracted position, a gap in the electrical connection between the RF generator and the RF electrode tip is formed, and
wherein a laser fiber is positioned within the first body shaft lumen and the laser fiber is configured to extend distally to cauterize tissue and retract proximally relative to the RF electrode tip, the laser fiber being thermally protected from the RF electrode tip when retracted within the lumen.

14. The medical device of claim 13, wherein the RF electrode tip further includes a ceramic substrate, the pair of RF electrodes being printed or chemically etched onto an exterior surface of the ceramic substrate.

15. The medical device of claim 13, wherein the RF electrode tip comprises a single ceramic tip, and the RF electrode tip is interference fitted to the distal end of the first body shaft.

16. The medical device of claim 13, wherein the energy delivery wire extends along a radially exterior surface of the first body shaft toward the handle.

17. The medical device of claim 13, wherein each RF electrode of the pair of RF electrodes extends in a direction transverse to a longitudinal axis of the first body shaft.

18. A medical device, comprising:
a handle including a handle lumen extending therethrough;
a first body shaft including a first body shaft lumen in direct communication with the handle lumen;
a second body shaft defining a second body shaft lumen, wherein the first body shaft is received within the second body shaft lumen;
an RF electrode tip interference fitted to a distal end of the first body shaft, wherein the RF electrode tip includes a lumen extending therethrough and in direct communication with the first body shaft lumen;
an RF generator plug electrically coupled with the RF electrode tip; and
an energy delivery wire electrically coupling the RF electrode tip to the RF generator,
wherein a proximal end of the handle further includes an opening in communication with the RF electrode tip, and the opening is configured to receive a laser fiber,
wherein the handle houses the RF generator plug, and the energy delivery wire extends along a radially exterior surface of the first body shaft and within the second body shaft lumen towards the handle, and
wherein the laser fiber is positioned within the first body shaft lumen and the laser fiber is configured to extend distally to cauterize tissue and retract proximally relative to the RF electrode tip, the laser fiber being thermally protected from the RF electrode tip when retracted within the lumen.

19. The medical device of claim 18, wherein the RF electrode tip comprises a single ceramic tip.

20. The medical device of claim 19, wherein the single ceramic tip is blunt.

* * * * *